United States Patent [19]

Gewirtz

[11] Patent Number: 5,612,212
[45] Date of Patent: Mar. 18, 1997

[54] SELECTIVE INHIBITION OF CELL PROLIFERATION BY VAV ANTISENSE OLIGONUCLEOTIDES

[75] Inventor: Alan M. Gewirtz, Philadelphia, Pa.

[73] Assignee: The University of Pennsylvania, Philadelphia, Pa.

[21] Appl. No.: 152,634

[22] Filed: Nov. 12, 1993

[51] Int. Cl.$^6$ ............................ C12N 5/10; C12N 15/85; C07H 21/00; C12Q 1/68
[52] U.S. Cl. ...................... 435/172.3; 435/6; 435/91.1; 435/91.3; 435/91.33; 435/91.4; 435/320.1; 435/375; 514/44; 536/23.1; 536/24.1; 536/24.3; 536/24.31; 536/24.33; 536/24.5; 536/25.1; 536/25.3; 536/24.32
[58] Field of Search ........................... 514/44; 536/24.5, 536/25.1, 23.1, 24.1, 24.3, 24.31, 24.32, 24.33, 25.3; 435/320.1, 172.3, 91.21, 91.3, 91.4, 6, 91.1, 91.33; 936/3, 6, 8, 22, 33, 34, 52–57, 70, 71, 76

[56] References Cited

U.S. PATENT DOCUMENTS 5,087,617 2/1992 Smith ...................................... 514/44
5,225,326 7/1993 Bresser et al. ............................ 435/6

FOREIGN PATENT DOCUMENTS 0496606 7/1992 European Pat. Off. ......... C12N 15/12

OTHER PUBLICATIONS

Katzav et al., "vav, A Novel Human Oncogene Derived from a Locus Ubiquitously Expressed in Hematopoietic Cells", *The Embo Journal*, 8, 2283–2290 (1989).
Coppola et al., "Mechanism of Activationof the vav Protooncogene", *Cell Growth & Differentiation* 2, 95–105 (Feb. 1991).
Katzav et al., "Loss of the Amino–Terminal Helix–Loop–Helix Domain of the vav Proto–Oncogene . . . " *Molecular and Cellular Biology* 11, No. 4, pp. 1912–1920 (Apr. 1991).
Hu et al., "Vav: A Potential Link between Tyrosine Kinases and Ras–like . . . " *BioEssays* 15, No. 3, pp. 179–182 (Mar. 1993).
Bustelo et al., "Developmental Expression of the vav Protooncogene", *Cell Growth & Differentiation* 4, 297–308 (Apr. 1993).
Zhang, R., et al. PNAS, vol. 91 (Dec. 1994) pp. 12755–12759.
E. Uhlmann et al. Chemical Reviews, vol. 90, #4 (Jun. '90) pp. 543–584.
P. Westermann et al. Biochem. Biomed. Ama, vol. 48 ('89) pp. 85–93.
B. Tseng et al. Cancer Gene Therapy, vol. 1 #1 (Mar. 1994) pp. 65–71.
C. Stein et al. Science, vol. 261 (20 Aug. 1993) pp. 1004–1012.
R. Weiss Science News, vol. 139 (Feb. 16, 1991) pp. 108–109.
W. James, Antiviral Chem. & Chemotherapy, vol. 2 #4 ('91) pp. 191–214.
E. McCulloch et al. Blood Cells, vol. 7 ('81) 63–77.
J. Curtis et al. J. Clin. Oncology, vol. 2 #4 (Apr. 1984) pp. 253–259.
R. Mulligan Science, vol. 260 (14 May 1993) pp. 926–932.
E. Wicksman The Faseb Journal, vol. 5 #5 (Mar. 15, 1991) p. A1443.
J. Adams et al. Oncogene, vol. 7 ('92) pp. 611–618.
D. Merrola et al. Biochem Biophys. Res. Comm., vol. 147 #1 ('87) pp. 288–294.
J. Wermur, Chem Rev. in Biochem. & Mol. Biol., vol. 26 (3/4) ('91) 227–59.
Y. Rojanasak, Adv. Dwg Reliv. Rev., vol. 18 ('96) 115–31.

*Primary Examiner*—Charles C. P. Rories
*Attorney, Agent, or Firm*—Seidel, Gonda, Lavorgna & Monaco, P.C.

[57] ABSTRACT

Antisense oligonucleotides specific for the vav proto-oncogene inhibit the proliferation of malignant, but not normal, myeloid cells. The oligonucleotides are therefore useful in the treatment of leukemias, in particular, as bone marrow purging agents. The vav antisense oligonucleotides also selectively inhibit the formation of erythroid cell colonies without effect on megakaryocyte and granulocyte/macrophage colony formation. The oligonucleotides are therefore useful in treating disorders characterized by an elevated hematocrit due to overproduction of erythrocytes.

18 Claims, No Drawings

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
( A ) LENGTH: 50 Nucleotides
( B ) TYPE: nucleic acid
( C ) STRANDEDNESS: single stranded
( D ) TOPOLOGY: linear ( x i ) SEQUENCE DESCRIPTION: SEQ ID NO:1:

AGCACCCGGC ACTGGATGAG CCAGTGGGTG CATTGGCGCC          40

ACAGCTCCAT          50

( 2 ) INFORMATION FOR SEQ ID NO:2:

( i ) SEQUENCE CHARACTERISTICS:
( A ) LENGTH: 18 Nucleotides
( B ) TYPE: nucleic acid
( C ) STRANDEDNESS: single stranded
( D ) TOPOLOGY: linear ( x i ) SEQUENCE DESCRIPTION: SEQ ID NO:2:

AAGGCACAGG AACTGGGA          18

( 2 ) INFORMATION FOR SEQ ID NO:3:

( i ) SEQUENCE CHARACTERISTICS:
( A ) LENGTH: 18 Nucleotides
( B ) TYPE: nucleic acid
( C ) STRANDEDNESS: single stranded
( D ) TOPOLOGY: linear ( x i ) SEQUENCE DESCRIPTION: SEQ ID NO:3:

TCCCAGTTCC TGTGCCTT          18

( 2 ) INFORMATION FOR SEQ ID NO:4:

( i ) SEQUENCE CHARACTERISTICS:
( A ) LENGTH: 18 Nucleotides
( B ) TYPE: nucleic acid
( C ) STRANDEDNESS: single stranded
( D ) TOPOLOGY: linear ( x i ) SEQUENCE DESCRIPTION: SEQ ID NO:4:

```
AGCTCGAAAG ACAGGGGA                                                                                   18
```

( 2 ) INFORMATION FOR SEQ ID NO:5:

( i ) SEQUENCE CHARACTERISTICS:
        ( A ) LENGTH: 21 Nucleotides
        ( B ) TYPE: nucleic acid
        ( C ) STRANDEDNESS: single stranded
        ( D ) TOPOLOGY: linear ( x i ) SEQUENCE DESCRIPTION: SEQ ID NO:5:

```
GGAGGTGATA TTTGAGAACT C                                                                               21
```

( 2 ) INFORMATION FOR SEQ ID NO:6:

( i ) SEQUENCE CHARACTERISTICS:
        ( A ) LENGTH: 21 Nucleotides
        ( B ) TYPE: nucleic acid
        ( C ) STRANDEDNESS: single stranded
        ( D ) TOPOLOGY: linear ( x i ) SEQUENCE DESCRIPTION: SEQ ID NO:6:

```
CCATCCAGCA GCATTTCTTG A                                                                               21
```

( 2 ) INFORMATION FOR SEQ ID NO:7:

( i ) SEQUENCE CHARACTERISTICS:
        ( A ) LENGTH: 26 Nucleotides
        ( B ) TYPE: nucleic acid
        ( C ) STRANDEDNESS: single stranded
        ( D ) TOPOLOGY: linear ( x i ) SEQUENCE DESCRIPTION: SEQ ID NO:7:

```
TTTGATGAAG ACCTGGTAGA GATTCG                                                                          26
```

SELECTIVE INHIBITION OF CELL PROLIFERATION BY VAV ANTISENSE OLIGONUCLEOTIDES

REFERENCE TO GOVERNMENT GRANT

The invention described herein was supported in part by National Institutes of Health grants CA54384 and CA51083. The United States Government has certain right in the invention.

FIELD OF THE INVENTION

The invention relates to antisense oligonucleotides to proto-oncogenes, in particular to antisense oligonucleotides to the vav gene, and the use of such oligonucleotides to selectively inhibit proliferation of certain cells.

BACKGROUND OF THE INVENTION

The vav proto-oncogene encodes a 95 kDa protein ($p95^{vav}$) which is thought to be expressed exclusively in hematopoietic cells of all lineages and stages of maturation. $p95^{vav}$ has a number of interesting motifs including several src homology, leucine zipper, zinc finger, helix-loop-helix, and guanine nucleotide releasing factor domains. The presence of these domains suggests that vav serves as a transcriptional activator and/or element of the signal transduction cascade. Indeed, $p95^{vav}$ functions as a guanine nucleotide releasing factor in ras activation by the T-cell receptor. However, vav's function in other lineages remains unclear.

The human proto-oncogene maps to chromosome region 19p12→19p13.2 (Martinerie et al., *Hum. Genet.* 86:65–68, 1990). The vav locus was first identified by virtue of its oncogenic activation during the course of gene transfer assays using human tumor DNAs (Katzav et al., *EMBO.*, 8:2283–2290, 1989). Molecular characterization of this oncogene allowed the isolation and characterization of its normal allele, the vav protooncogene (Coppola et al., *Cell. Growth & Differ.*, 2:95–105, 1991; Katzav et al., *Mol. Cell. Bio.*, 11:1912–1920, 1991). The vav proto-oncogene directs the synthesis of a 3.0 kb transcript that has been found to be specifically expressed in cells of hematopoietic origin. Removal of the helix-loop-helix sequences results in the malignant activation of the $p95^{vav}$ protein (Id.).

The cDNA nucleotide sequence of the vav gene and predicted 797 amino acid polypeptide are provided by Katzav et al., 1989, supra. The vav proto-oncogene nucleotide sequence of the 5' untranslated region up-stream of the translation initiation codon is disclosed in Katzav et al., 1991, Supra.

Analysis of vav gene transcripts in human cell lines has indicated that the gene is expressed in cells of hematopoietic origin; no vav gene transcripts could be observed in epithelial, mesenchymal or neuroectodermal cells (Katzav et al., 1989, supra). Lymphoid, myeloid and erythroid cell lines contained comparable levels of vav gene transcripts (Katzav et al., 1989, supra). However, the therapeutic utility of regulating vav expression has not heretofore been explored.

SUMMARY OF THE INVENTION

The invention provides antisense oligonucleotides and pharmaceutical compositions thereof. A pharmaceutical composition comprises a pharmaceutically acceptable carrier and an antisense oligonucleotide specific for vav, as hereinafter defined.

According to one embodiment, the oligonucleotide has a nucleotide sequence capable of forming a stable duplex with a portion of an mRNA transcript of the vav proto-oncogene.

The oligonucleotide is generally at least an 8-mer oligonucleotide, that is, the oligonucleotide is an oligomer containing at least 8 nucleotide residues, more preferably at least about 12 nucleotides. The preferred maximum size of the oligonucleotide is about 60 nucleotides, more preferably about 50 nucleotides. The oligomer is preferably an oligodeoxynucleotide.

While oligonucleotides smaller than 12-mers may be utilized, they are statistically more likely to hybridize with non-targeted sequences, and for this reason may be less specific. In addition, a single mismatch may destabilize the hybrid. While oligonucleotides larger than 40-mers may be utilized, uptake may become more difficult without specialized vehicles or oligonucleotide carriers. Moreover, partial matching of long sequences may lead to non-specific hybridization, and non-specific effects. Most preferably, the oligonucleotide is a 15- to 40-mer oligodeoxynucleotide, more advantageously an 18- to 30-mer.

While in principle oligonucleotides having a sequence complementary to any region of the vav mRNA find utility in the present invention, preferred are oligonucleotides capable of forming a stable duplex with a portion of the vav transcript lying within about 50 nucleotides (preferably within about 40 nucleotides) upstream (the 5' direction), or about 50 (preferably 40) nucleotides downstream (the 3' direction) from the translation initiation codon. Also are preferred are oligonucleotides which are capable of forming a stable duplex with a portion of a vav mRNA transcript including the translation initiation codon.

The invention provides a method of treating hematological neoplasms in vivo or ex vivo comprising administering to an individual or cells harvested from the individual an effective amount of vav antisense oligonucleotide.

The invention is also a method for inhibiting proliferation of erythroid cells comprising administering to a host in need of such treatment an effective amount of an antisense oligonucleotide specific for vav.

The invention is also a method for purging bone marrow of neoplastic cells. Bone marrow aspirated from an individual afflicted with a hematologic neoplasm is treated with an effective amount of vav antisense oligonucleotide, and the thus-treated cells are then returned to the body of the afflicted individual.

The invention is also a method for inhibiting solid tumors comprising administering to a host in need of such treatment an effective amount of an antisense oligonucleotide specific for vav. In particular, the invention comprises a method for inhibiting solid tumors characterized by low level expression of vav. Solid tumors characterized by low level vav expression include lung tumors, for example.

According to another embodiment, the invention is an artificially-constructed gene comprising a transcriptional promotor segment and a segment containing vav DNA in inverted orientation such that transcription of the artificially-constructed gene produces RNA complementary to a portion of an mRNA transcript of the vav gene. The gene may be introduced into neoplastic cells to inhibit the proliferation of those cells. The artificially-constructed gene may be introduced into the neoplastic cells by, for example, transfection, transduction with a viral vector, or microinjection.

Definitions

An "antisense oligonucleotide specific for vav" or "vav antisense oligonucleotide" is an oligonucleotide having a sequence (i) capable of forming a stable triplex with a portion of the vav protooncogene, or (ii) capable of forming a stable duplex with a portion of an mRNA transcript of the vav protooncogene.

The term "oligonucleotide" as used herein includes linear oligomers of natural or modified monomers or linkages, including deoxyribonucleosides, ribonucleosides, α-anomeric forms thereof, polyamide nucleic acids, and the like, capable of specifically binding to a target polynucleotide by way of a regular pattern of monomer-to-monomer interactions, such as Watson-Crick type of base pairing, Hoogsteen or reverse Hoogsteen types of base pairing, or the like. Usually, monomers are linked by phosphodiester bonds or analogs thereof to form oligonucleotides ranging in size from a few monomeric units, e.g., 3–4, to several hundreds of monomeric units. Analogs of phosphodiester linkages include: phosphorothioate, phosphorodithioate, phosphoroselenoate, phosphorodiselenoate, phosphoroanilothioate, phosphoranilidate, phosphoramidate, and the like, as more fully described below. As used herein, "nucleoside" includes the natural nucleosides, including 2'-deoxy and 2'-hydroxyl forms, e.g., as described in Kornberg and Baker, *DNA Replication*, 2nd Ed. (Freeman, San Francisco, 1992). "Analogs" in reference to nucleosides includes synthetic nucleosides having modified base moieties and/or modified sugar moieties, e.g., described generally by Scheit, *Nucleotide Analogs*. (John Wiley, New York, 1980). Such analogs include synthetic nucleosides designed to enhance binding properties, e.g., duplex or triplex stability, specificity, or the like.

The term "phosphorothioate oligonucleotide" means an oligonucleotide wherein one or more of the internucleotide linkages is a phosphorothioate group,

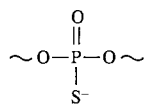

as opposed to the phosphodiester group

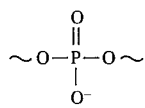

which is characteristic of unmodified oligonucleotides.

By "alkylphosphonate oligonucleoside" is meant an oligonucleotide wherein one or more of the internucleotide linkages is an alkylphosphonate group,

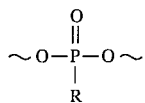

wherein R is an alkyl group, preferably methyl or ethyl.

"Stability" in reference to duplex or triplex formation roughly means how tightly an antisense oligonucleotide binds to its intended target sequence; more precisely, it means the free energy of formation of the duplex or triplex under physiological conditions. Melting temperature under a standard set of conditions, e.g., as described below, is a convenient measure of duplex and/or triplex stability. Preferably, antisense oligonucleotides of the invention are selected that have melting temperatures of at least 50° C. under the standard conditions set forth below; thus, under physiological conditions and the preferred concentrations, duplex or triplex formation will be substantially favored over the state in which the antisense oligonucleotide and its target are dissociated. It is understood that a stable duplex or triplex may in some embodiments include mismatches between base pairs and/or among base triplets in the case of triplexes. Preferably, antisense oligonucleotides of the invention form perfectly matched duplexes and/or triplexes with their target polynucleotides.

The term "downstream" when used in reference to a direction along a nucleotide sequence means the 5'→3' direction. Similarly, the term "upstream" means the 3'→5' direction.

The term "vav mRNA transcript" means the presently known mRNA transcript of the vav gene and all variations thereof, or any further transcripts which may be elucidated.

DETAILED DESCRIPTION OF THE INVENTION

The cDNA nucleotide sequence of the vav gene and predicted 797 amino acid polypeptide are provided by Katzav et al., 1989, supra. The nucleotide sequence of the 5' untranslated region upstream of the vav translation initiation codon is disclosed in Katzav et al., 1991, supra. The entire disclosures of Katzav et al. 1989 and 1991 are incorporated herein by reference. The translation initiation codon ATG is preceded by a 5'-untranslated region of about 253 nucleotides, containing three transcription initiation sites and consensus sequences for Sp1, AP-1 and AP-2 transcription factors. The termination codon TGA is followed by a 3'-untranslated region spanning about 264 nucleotides, including a consensus polyadenylation signal sequence near the 3' end.

Antisense oligonucleotides specific for vav display a striking differential toxicity to different hematologic cell types. Vav antisense oligonucleotides inhibit erythroid colony formation, but not megakaryocyte or granulocyte/macrophage colony formation, by normal cells. This is surprising in view of the finding by Katzav et al., 1989, supra, that erythroid and myeloid cell lines contain comparable levels of vav gene transcripts. This unexpected pharmaceutically significant differential sensitivity renders the instant oligonucleotides useful in treating disorders characterized by elevated production of red blood cells.

While the vav antisense oligonucleotides have no effect on granulocyte/macrophage colony formation by normal cells, the oligonucleotides inhibit the formation of such colonies in the bone marrow of patients afflicted with leukemia. The concentration of oligonucleotide administered may be selected to minimize the impact on the formation of normal erythroid cells, which are sensitive to vav antisense inhibition. This pharmaceutically significant differential sensitivity renders vav antisense oligonucleotides useful in the treatment of hematologic neoplasms, which comprise malignancies of myeloid cell origin.

I have also surprisingly found that non-hematologic solid tumors are sensitive to growth inhibition by vav antisense oligonucleotides. In particular, I have found that vav antisense oligonucleotides inhibit the growth of lung tumors. Thus, the present invention provides a method for inhibiting solid tumors. The fact that inhibition was obtained may be viewed as surprising given the low level of vav expression in lung cancer which I have found. Nevertheless, it now appears that this low level of vav expression has biological importance in solid tumors, in which vav is expressed only in low levels.

Target polynucleotides may be single-stranded or double-stranded DNA or RNA; however, single-stranded DNA or RNA targets are preferred. It is understood that the target to which the vav antisense oligonucleotides of the invention are directed include allelic forms of the vav proto-oncogene. There is substantial guidance in the literature for selecting particular sequences for antisense oligonucleotides given a knowledge of the sequence of the target polynucleotide, e.g., Peyman and Ulmann, *Chemical Reviews,* 90:543–584, 1990; Crooke, Ann. *Rev. Pharmacal. Toxicol.,* 32:329–376 (1992); and Zamecnik and Stephenson, Proc. Natl. Acad. Sci., 75:280–284 (1974). Preferably, the sequences of vav antisense compounds are selected such that the G-C content is at least 60%. Preferred proto-oncogene mRNA targets include the 5' cap site, tRNA primer binding site, the initiation codon site, the mRNA donor splice site, and the mRNA acceptor splice site, e.g., Goodchild et al., U.S. Pat. No. 4,806,463.

Where the target polynucleotide comprises the vav mRNA transcript, oligonucleotides complementary to and hybridizable with any portion of the transcript are, in principle, effective for inhibiting translation, and capable of inducing the effects herein described. It is believed that translation is most effectively inhibited by blocking the mRNA at a site at or near the initiation codon. Thus, oligonucleotides complementary to the 5'-region of the vavMRNA transcript are preferred. Oligonucleotides complementary to the vav MRNA, including the initiation codon (the first codon at the 5' end of the translated portion of the vav transcript), or codons adjacent the initiation codon, are preferred.

While antisense oligomers complementary to the 5'-region of the vav transcript are preferred, particularly the region including the initiation codon, it should be appreciated that useful antisense oligomers are not limited to those complementary to the sequences found in the translated portion of the MRNA transcript, but also includes oligomers complementary to nucleotide sequences contained in, or extending into, the 5'-and 3'-untranslated regions.

The following 50-mer oligodeoxynucleotide is complementary to the vav MRNA transcript beginning with the initiation codon of the transcript and extending downstream thereof: SEQ ID NO:1.

Smaller oligomers based upon the above sequence, in particular, oligomers hybridizable to segments of the vav message containing the initiation codon, may be utilized. Particularly preferred are oligomers containing at least 12 nucleotides, having a nucleotide sequence corresponding to a portion of SEQ ID NO:1.

Antisense oligonucleotides of the invention may comprise any polymeric compound capable of specifically binding to a target polynucleotide by way of a regular pattern of monomer-to-nucleoside interactions, such as Watson-Crick type of base pairing, Hoogsteen or reverse Hoogsteen types of base pairing, or the like. Antisense compounds of the invention may also contain pendent groups or moieties, either as part of or separate from the basic repeat unit of the polymer, to enhance specificity, nuclease resistance, delivery, or other property related to efficacy, e.g., cholesterol moieties, duplex intercalators such as acridine, poly-L-lysine, "end-capping" with one or more nuclease-resistant linkage groups such as phosphorothioate, and the like.

For example, it is known that enhanced lipid solubility and/or resistance to nuclease digestion results by substituting an alkyl group or alkoxy group for a phosphate oxygen in the internucleotide phosphodiester linkage to form an alkylphosphonate oligonucleoside or alkylphosphotriester oligonucleotide. Non-ionic oligonucleotides such as these are characterized by increased resistance to nuclease hydrolysis and/or increased cellular uptake, while retaining the ability to formstable complexes with complementary nucleic acid sequences. The alkylphosphonates, in particular, are stable to nuclease cleavage and soluble in lipid. The preparation of alkylphosphonate oligonucleosides is disclosed in Tso et al., U.S. Pat. No. 4,469,863.

Preferably, nuclease resistance is conferred on the antisense compounds of the invention by providing nuclease-resistant internucleosidic linkages. Many such linkages are known in the art, e.g., phosphorothioate: Zon and Geiser, *Anti-Cancer Drug Design,* 6:539–568 (1991); Stec et al., U.S. Pat. No. 5,151,510; Hirschbein, U.S. Pat. No. 5,166, 387; Bergot, U.S. Pat. No. 5,183,885; phosphorodithioates: Marshall et al., *Science,* 259:1564–1570 (1993); Caruthers and Nielsen, International application PCT/US89/02293; phosphoramidates, e.g., —OP(=O)—(NR$^1$R$^2$)—O— with R$^1$ and R$^2$ hydrogen or C$_1$_C$_3$ alkyl; Jager et al., *Biochemistry,* 27:7237–7246 (1988); Froehler et al., International application PCT/US90/03138; peptide nucleic acids: Nielsen et al., *Anti-Cancer Drug Design,* 8: 53–63 (1993), International application PCT/-EP92/01220; methylphosphonates: Miller et al., U.S. Pat. No. 4,507,433, Ts'o et al., U.S. Pat. No. 4,469,863; Miller et al., U.S. Pat. No. 4,757, 055; and P-chiral linkages of various types, especially phosphorothioates, Stec et al., European patent application 506,242 (1992) and Lesnikowski, *Bioorganic Chemistry,* 21:127–155 (1993). Additional nuclease linkages include phosphoroselenoate, phosphorodiselenoate, phosphoroanilothioate, phosphoranilidate, alkylphosphotriester such as methyl- and ethylphosphotriester, carbonate such as carboxymethyl ester, carbamate, morpholino carbamate, 3'-thioformacetal, silyl such as dialkyl(C$_1$_C$_6$)— or diphenylsilyl, sulfamate ester, and the like. Such linkages and methods for introducing them into oligonucleotides are described in many references, e.g., reviewed generally by Peyman and Ulmann, *Chemical Reviews* 90:543–584 (1990); Milligan et al., *J. Med. Chem.,* 36:1923–1937 (1993); Matteucci et al., International application PCT/US91/06855.

Resistance to nuclease digestion may also be achieved by modifying the internucleotide linkage at both the 5'and 3'termini with phosphoroamidites according to the procedure of Dagle et al., *Nucl. Acids Res.* 18, 4751–4757 (1990).

Preferably, phosphorus analogs of the phosphodiester linkage are employed in the compounds of the invention, such as phosphorothioate, phosphorodithioate, phosphoramidate, or methylphosphonate. More preferably, phosphorothioate is employed as the nuclease resistant linkage.

Phosphorothioate oligonucleotides contain a sulfur-for-oxygen substitution in the internucleotide phosphodiester bond. Phosphorothioate oligonucleotides combine the properties of effective hybridization for duplex formation with substantial nuclease resistance, while retaining the water solubility of a charged phosphate analogue. The charge is believed to confer the property of cellular uptake via a receptor (Loke et al., *Proc. Natl. Acad. Sci.,* 86, 3474–3478 (1989)).

It is understood that in addition to the preferred linkage groups, compounds of the invention may comprise additional modifications, e.g., boronated bases, Spielvogel et al., U.S. Pat. No. 5,130,302; cholesterol moieties, Shea et al., *Nucleic Acids Research,* 18:3777–3783 (1990) or Letsinger et al., *Proc. Natl. Acad. Sci.,* 86:6553–6556 (1989); and 5-propynyl modification of pyrimidines, Froehler et al., *Tetrahedron Lett.,* 33:5307–5310 (1992).

Preferably, antisense compounds of the invention are synthesized by conventional means on commercially available automated DNA synthesizers, e.g., an Applied Biosystems (Foster City, Calif.) model 380B, 392 or 394 DNA/RNA synthesizer. Preferably, phosphoramidite chemistry is employed, e.g., as disclosed in the following references: Beaucage and Iyer, *Tetrahedron*, 48:2223–2311 (1992); Molko et. al., U.S. Pat. No. 4,980,460; Koster et al., U.S. Pat. No. 4,725,677; Caruthers et al., U.S. Pat. Nos. 4,415,732; 4,458,066; and 4,973,679.

In embodiments where triplex formation is desired, there are constraints on the selection of target sequences. Generally, third strand association via Hoogsteen type of binding is most stable along homopyri-midine-homopurine tracks in a double stranded target. Usually, base triplets form in T-A*T or C-G*C motifs (where "-" indicates Watson-Crick pairing and "*" indicates Hoogsteen type of binding); however, other motifs are also possible. For example, Hoogsteen base pairing permits parallel and antiparallel orientations between the third strand (the Hoogsteen strand) and the purinerich strand of the duplex to which the third strand binds, depending on conditions and the composition of the strands. There is extensive guidance in the literature for selecting appropriate sequences, orientation, conditions, nucleoside type (e.g., whether ribose or deoxyribose nucleosides are employed), base modifications (e.g., methylated cytosine, and the like) in order to maximize, or otherwise regulate, triplex stability as desired in particular embodiments, e.g., Roberts et el., *Proc. Natl. Acad. Sci.*, 88:9397–9401 (1991); Roberts et al., *Science*, 258:1463–1466 (1992); Distefano et al., *Proc. Natl. Acad. Sci.*, 90:1179–1183 (1993); Mergny et al., *Biochemistry*, 30:9791–9798 (1992); Cheng et al., *J. Am. Chem. Soc.*, 114:4465–4474 (1992); Beal and Dervan, *Nucleic Acids Research*, 20:2773–2776 (1992); Beal and Dervan, *J. Am. Chem. Soc.*, 114:4976–4982; Giovannangeli et al., *Proc. Natl. Acad. Sci.*, 89:8631–8635 (1992); Moser and Dervan, *Science*, 238:645–650 (1987); McShan et al., *J. Biol. Chem.*, 267: 5712–5721 (1992); Yoon et el., *Proc. Natl. Acad. Sci.*, 89:3840–3844 (1992); and Blume et al., *Nucleic Acids Research*, 20:1777–1784 (1992).

The length of the oligonucleotide moieties is sufficiently large to ensure that specific binding will take place only at the desired target polynucleotide and not at other fortuitous sites, as explained in many references, e.g., Rosenberg et al., International application PCT/US92/05305; or Szostak et al., *Meth. Enzymol*, 68:419–429 (1979). The upper range of the length is determined by several factors, including the inconvenience and expense of synthesizing and purifying oligomers greater than about 30–40 nucleotides in length, the greater tolerance of longer oligonucleotides for mismatches than shorter oligonucleotides, whether modifications to enhance binding or specificity are present, whether duplex or triplex binding is desired, and the like. Usually, antisense compounds of the invention have lengths in the range of about 12 to 60 nucleotides. More preferably, antisense compounds of the invention have lengths in the range of about 15 to 40 nucleotides; and most preferably, they have lengths in the range of about 18 to 30 nucleotides.

In general, the antisense oligonucleotides used in the practice of the present invention will have a sequence which is completely complementary to a selected portion of the target polynucleotide. Absolute complementarity is not however required, particularly in larger oligomers. Thus, reference herein to a "nucleotide sequence complementary to" a target polynucleotide does not necessarily mean a sequence having 100% complementarity with the target segment. In general, any oligonucleotide having sufficient complementarity to form a stable duplex with the target (e.g. the vav mRNA) that is an oligonucleotide which is "hybridizable" is suitable. Stable duplex formation depends on the sequence and length of the hybridizing oligonucleotide and the degree of complementarity with the target polynucleotide. Generally, the larger the hybridizing oligomer, the more mismatches may be tolerated. More than one mismatch probably will not be tolerated for antisense oligomers of less than about 21 nucleotides. One skilled in the art may readily determine the degree of mismatching which may be tolerated between any given antisense oligomer and the target sequence, based upon the melting point, and therefore the thermal stability, of the resulting duplex.

Preferably, the thermal stability of hybrids formed by the antisense oligonucleotides of the invention are determined by way of melting, or strand dissociation, curves. The temperature of fifty percent strand dissociation is taken as the melting temperature, $T_m$, which, in turn, provides a convenient measure of stability. $T_m$ measurements are typically carried out in a saline solution at neutral pH with target and antisense oligonucleotide concentrations at between about 1.0–2.0 µM. Typical conditions are as follows: 150 mM NaCl and 10 mM $MgCl_2$ in a 10 mM sodium phosphate buffer (pH 7.0) or in a 10mM Tris-HCl buffer (pH 7.0). Data for melting curves are accumulated by heating a sample of the antisense oligonucleotide/target polynucleotide complex from room temperature to about 85°–90° C. As the temperature of the sample increases, absorbance of 260 nm light is monitored at 1° C. intervals, e.g., using a Cary (Australia) model 1E or a Hewlett-Packard (Palo Alto, Calif.) model HP 8459 UV/VIS spectrophotometer and model HP 89100A temperature controller, or like instruments. Such techniques provide a convenient means for measuring and comparing the binding strengths of antisense oligonucleotides of different lengths and compositions.

Pharmaceutical compositions of the invention include a pharmaceutical carrier that may contain a variety of components that provide a variety of functions, including regulation of drug concentration, regulation of solubility, chemical stabilization, regulation of viscosity, absorption enhancement, regulation of pH, and the like. The pharmaceutical carrier may comprise a suitable liquid vehicle or excipient and an optional auxiliary additive or additives. The liquid vehicles and excipients are conventional and commercially available. Illustrative thereof are distilled water, physiological saline, aqueous solutions of dextrose, and the like. For water soluble formulations, the pharmaceutical composition preferably includes a buffer such as a phosphate buffer, or other organic acid salt, preferably at a pH of between about 7 and 8. For formulations containing weakly soluble antisense compounds, microemulsions may be employed, for example by using a nonionic surfactant such as polysorbate 80 in an amount of 0.04–0.05% (w/v), to increase solubility. Other components may include antioxidants, such as ascorbic acid, hydrophilic polymers, such as, monosaccharides, disaccharides, and other carbohydrates including cellulose or its derivatives, dextrins, chelating agents, such as EDTA, and like components well known to those in the pharmaceutical sciences, e.g., *Remington's Pharmaceutical Science*, latest edition (Mack Publishing Company, Easton, Pa.).

Antisense compounds of the invention include the pharmaceutically acceptable salts thereof, including those of alkaline earths, e.g., sodium or magnesium, ammonium or $NX_4^+$, wherein X is $C_1$–$C_4$ alkyl Other pharmaceutically acceptable salts include organic carboxylic acids such as acetic, lactic, tartaric, malic, isethionic, lactobionic, and succinic acids; organic sulfonic acids such as methanesulfonic, ethanesulfonic, and benzenesulfonic; and inorganic acids such as hydrochloric, sulfuric, phosphoric, and sulfamic acids. Pharmaceutically acceptable salts of a compound having a hydroxyl group include the anion of such compound in combination with a suitable cation such as $Na^+$, $NH_4^+$, or the like.

The vav antisense oligonucleotides are preferably administered parenterally, most preferably intravenously. The vehicle is designed accordingly. Alternatively, oligonucleotide may be administered subcutaneously via controlled release dosage forms.

In addition to administration with conventional carriers, the antisense oligonucleotides may be administered by a variety of specialized oligonucleotide delivery techniques. Sustained release systems suitable for use with the pharmaceutical compositions of the invention include semi-permeable polymer matrices in the form of films, microcapsules, or the like, comprising polylactides, copolymers of L-glutamic acid and gamma-ethyl-L-glutamate, poly(2-hydroxyethyl methacrylate), and like materials, e.g., Rosenberg et al., International application PCT/US92/05305.

The oligonucleotides may be encapsulated in liposomes for therapeutic delivery, as described for example in *Liposome Technology*, Vol. II, *Incorporation of Drugs, Proteins, and Genetic Material*, CRC Press. The oligonucleotide, depending upon its solubility, may be present both in the aqueous layer and in the lipidic layer, or in what is generally termed a liposomic suspension. The hydrophobic layer, generally but not exclusively, comprises phospholipids such as lecithin and sphingomyelin, steroids such as cholesterol, ionic surfactants such as diacetylphosphate, stearylamine, or phosphatidic acid, and/or other materials of a hydrophobic nature.

The oligonucleotides may be conjugated to poly(L-lysine) to increase cell penetration. Such conjugates are described by Lemaitre et al., *Proc. Natl. Acad. Sci. USA*, 84, 648–652 (1987). The procedure requires that the 3'-terminal nucleotide be a ribonucleotide. The resulting aldehyde groups are then randomly coupled to the epsilon-amino groups of lysine residues of poly(L-lysine) by Schiff base formation, and then reduced with sodium cyanoborohydride. This procedure converts the 3'-terminal ribose ring into a morpholine structure antisense oligomers.

Antisense compounds of the invention also include conjugates of such oligonucleotides with appropriate ligand-binding molecules. The oligonucleotides may be conjugated for therapeutic administration to ligand-binding molecules which recognize cell-surface molecules, such as according to International Patent Application WO 91/04753. The ligand-binding molecule may comprise, for example, an antibody against a cell surface antigen, an antibody against a cell surface receptor, a growth factor having a corresponding cell surface receptor, an antibody to such a growth factor, or an antibody which recognizes a complex of a growth factor and its receptor. Methods for conjugating li-gand-binding molecules to oligonucleotides are detailed in WO 91/04753.

In particular, the growth factor to which the antisense oligonucleotide may be conjugated, may comprise transferrin or folate. Transferrin-polylysine-oligonucleotide complexes or folate-polylysine-oligonucleotide complexes may be prepared for uptake by cells expressing high levels of transferrin or folate receptor. The preparation of transferrin complexes as carriers of oligonucleotide uptake into cells is described by Wagner et al., *Proc. Natl. Acad. Sci. USA* 87, 3410–3414 (1990). Inhibition of leukemia cell proliferation by transferrin receptor-mediated uptake of c-myb antisense oligonucleotides conjugated to transferrin has been demonstrated by Citro et al., *Proc. Natl. Acad. Sci. USA*, 89, 7031–7035 (1992). Cellular delivery of folate-macromolecule conjugates via folate receptor endocytosis, including delivery of an antisense oligonucleotide, is described by Low et al., U.S. Pat. No. 5,108,921. Also see, Leamon et al., *Proc. Natl. Acad. Sci.* 88, 5572 (1991).

The vav antisense oligonucleotides inhibit human erythropoiesis, as indicated by inhibition of erythroid colony formation. However, they do not appear to inhibit proliferation of normal cells of other lineages, such as colony forming unit-granulocyte-macrophage cells (CFU-GM) and colony forming unit-megakaryocyte cells (CFU-MEG). CFU-GM cells and CFU-MEG cells are the progenitors of blood granulocytes and platelets, respectively. This pharmaceutically significant differential sensitivity makes the instant oligonucleotides useful in treating disorders characterized by elevated production of red blood cells.

The vav antisense oligonucleotides are believed useful in the treatment of any one of a variety of conditions characterized by an elevated hematocrit due to overproduction of erythrocytes. One such disorder, polycythemia, may arise from a variety of causes and is classified as either relative, secondary or primary polycythemia.

In relative polycythemia, the red cell mass is normal. Plasma volume is decreased. The increase in erythrocytes is therefore a concentration effect. Relative polycythemia is associated with diabetic acidosis, diarrhea, or diabetes insipidus. It is also associated with the intake of diuretics.

In secondary polycythemia, red cell mass is increased secondarily to elevated erythropoietin (EPO) production. This occurs in individuals who have located to higher altitudes, since decreased oxygen simulates anemia, which is a triggering signal for increase of erythrocyte production. Secondary polycythemia may also occur in patients who have significant pulmonary or cardiac disfunction. Decreased oxygen delivery to tissues simulates anemia which triggers a signal to increase erythrocyte production. Secondary polycythemia may also occur in individuals who have tumors which are capable of synthesizing EPO, as in hypernephroma, cerebellar hemangioma and uterine leiomyoma.

Primary polycythemia is characterized by an increase in red cell mass, with either normal or decreased EPO levels. Primary polycythemia occurs in the myeloproliferative disorders, in particular polycythemia vera (PV). Disorders such as PV are true stem cell disorders. Accordingly, the white blood cell count and platelet count may be elevated. However, control of erythrocyte production is the primary objective in management of PV. Control of PV is usually effected by phlebotomy in secondary causes (if treatment of the primary disease is ineffective), and by a combination of phlebotomy and chemotherapy. Chemotherapeutic treatment of PV typically utilizes alkylating agents such as busulfan, melphalan, cyclophosphamide, chlorambucil or radioactive phosphorous in the form of sodium phosphate-$^{32}$P.

The rapid fluid shifts imposed by phlebotomy in the treatment of PV can be dangerous for patients with cardiac/pulmonary disease. Phlebotomy is also associated with a significant risk of fatal thrombosis. (Burk et al., *Semin. Hematol.* 23, 132 (1986). Control of erythrocyte production by administration of the vav antisense oligomers of the present invention is an attractive alternative to phlebotomy and chemotherapy.

The antisense oligonucleotides of the invention are further useful in the treatment of hematologic malignancies. Hematologic neoplastic cells believed sensitive to the instant vav antisense oligonucleotides include, for example, myeloid leukemia cells. The appearance of these cells in the bone marrow and elsewhere in the body is associated with various disease conditions, such as all of the various French-American-British (FAB) subtypes of acute myeloid leukemia (AML), and chronic myeloid leukemia (CML).

CML, in particular, is characterized by abnormal proliferation of immature granulocytes—neutrophils, eosinophils, and basophils—in the blood, the bone marrow, the spleen, the liver, and sometimes other tissues. The essential feature is accumulation of granulocytic precursors in these tissues. The patient who presents symptoms will characteristically have more than 20,000 white blood cells per μl, and the count may exceed 400,000. Virtually all CML patients will develop "blast crisis", the terminal stage of the disease during which immature blast cells rapidly proliferate, leading to patient death.

Malignant, but not normal, myeloid cell colony formation is sensitive to inhibition by vav antisense oligonucleotide. This differential sensitivity makes possible the use of vav antisense oligonucleotides as antileukemic agents, in particular, in purging neoplastic cells from bone marrow.

A preferred method of administration of oligonucleotide comprises either systemic or regional perfusion, as is appropriate. According to a method of regional perfusion, the afferent and efferent vessels supplying the extremity containing the lesion are isolated and connected to a low-flow perfusion pump in continuity with an oxygenator and a heat exchanger. The iliac vessels may be used for perfusion of the lower extremity. The axillary vessels are cannulated high in the axilla for upper extremity lesions. Oligonucleotide is added to the perfusion circuit, and the perfusion is continued for an appropriate time period, e.g., one hour. Perfusion rates of from 100 to 150 ml/minute may be employed for lower extremity lesions, while half that rate should be employed for upper extremity lesions. Systemic heparinization may be used throughout the perfusion, and reversed after the perfusion is complete. This isolation perfusion technique permits administration of higher doses of chemotherapeutic agent than would otherwise be tolerated upon infusion into the arterial or venous systemic circulation.

For systemic infusion, the oligonucleotides are preferably delivered via a central venous catheter, which is connected to an appropriate continuous infusion device. Indwelling catheters provide long term access to the intravenous circulation for frequent administration of drugs over extended time periods. They are generally surgically inserted into the external cephalic or internal jugular vein under general or local anesthesia. The subclavian vein is another common site of catheterization. The infuser pump may be external, or may form part of an entirely implantable central venous system such as the INFUSAPORT system available from Infusaid Corp., Norwood, MA and the PORT-A-CATH system available from Pharmacia Laboratories, Piscataway, N.J. These devices are implanted into a subcutaneous pocket under local anesthesia. A catheter, connected to the pump injection port, is threaded through the subclavian vein to the superior vena cava. The implant contains a supply of oligonucleotide in a reservoir which may be replenished as needed by injection of additional drug from a hypodermic needle through a self-sealing diaphragm in the reservoir. Completely implantable infusers are preferred, as they are generally well accepted by patients because of the convenience, ease of maintenance and cosmetic advantage of such devices.

As an alternative to treatment with exogenous oligonucleotide, antisense oligonucleotide synthesis may be induced in situ by local treatment of the targeted neoplastic cells with a vector containing an artificially-constructed gene comprising a transcriptional promotor and vav D1 DNA in inverted orientation. The vav DNA for insertion into the artificial gene in inverted orientation comprises cDNA which may be prepared, for example, by reverse transcriptase polymerase chain reaction from RNA using primers derived from the published vav cDNA sequence. Upon transcription, the inverted vav gene segment, which is complementary to the vav mRNA, is produced in situ in the targeted cell. The endogenously produced RNA hybridizes to vav mRNA, resulting in interference with vav function and inhibition of the proliferation of the targeted cell.

The promotor segment of the artificially-constructed gene serves as a signal conferring expression of the inverted vav sequence which lies downstream thereof. It will include all of the signals necessary for initiating transcription of the sequence. The promotor may be of any origin as long as it specifies a rate of transcription which will produce sufficient antisense mRNA to inhibit the expression of the vav gene, and therefore the proliferation of the targeted malignant cells. Preferably, a highly efficient promotor for such as a viral promotor is employed. Other sources of potent promotors include cellular genes that are expressed at high levels. The promotor segment may comprise a constitutive or a regulatable promotor.

The artificial gene may be introduced by any of the methods described in U.S. Pat. No. 4,740,463, incorporated herein by reference. One technique is transfection, which can be done by several different methods. One method of transfection involves the addition of DEAE-dextran to increase the uptake of the naked DNA molecules by a recipient cell. See McCutchin, J. H. and Pagano, J. S., *J. Natl. Cancer Inst.* 41, 351–7 (1968). Another method of transfection is the calcium phosphate precipitation technique which depends upon the addition of $Ca^{++}$ to a phosphate-containing DNA solution. The resulting precipitate apparently includes DNA in association with calcium phosphate crystals. These crystals settle onto a cell monolayer; the resulting apposition of crystals and cell surface appears to lead to uptake of the DNA. A small proportion of the DNA taken up becomes expressed in a transfectant, as well as in its clonal descendants. See Graham, F. L. and van der Eb, A. J., *Virology* 52, 456–467 (1973) and *Virology* 54, 536–539 (1973).

Transfection may also be carried out by cationic phospholipid-mediated delivery. In particular, polycationic liposomes can be formed from N-[1-(2,3-dioleyloxy)propyl]-N, N,N-trimethylammonium chloride (DOTMA). See Felgner et al., *Proc. Natl. Acad. Sci.*, 84, 7413–7417 (1987) (DNA-transfection); Malone et al., *Proc. Natl. Acad. Sci.*, 86, 6077–6081 (1989) (RNA-transfection).

Alternatively, the artificially-constructed gene can be introduced in to cells, in vitro or in vivo, via a transducing viral vector. See Tabin et al., *Mol. Cel. Biol.* 2, 426–436 (1982). Use of a retrovirus, for example, will infect a variety of cells and cause the artificial gene to be inserted into the genome of infected cells. Such infection coula either be accomplished with the aid of a helper retrovirus, which would allow the virus to spread through the organism, or the antisense retrovirus could be produced in a helper-free system, such as ψ2-like cells (See Mann et al., *Cell* 33, 153–160, 1983) that package amphotropic viruses. A helper-free virus might be employed to minimize spread throughout the organism. Viral vectors in addition to retroviruses can also be employed, such as papovaviruses, SV40-like viruses, or papilloma viruses. The use of retroviruses for gene transfer has been reviewed by Eglitis and Anderson, *BioTechniques* 6, 608–614 (1988).

Vesicle fusion could also be employed to deliver the artificial gene. Vesicle fusion may be physically targeted to the malignant cells if the vesicle were approximately designed to be taken up by those cells. Such a delivery system would be expected to have a lower efficiency of integration and expression of the artificial gene delivered, but would have a higher specificity than a retroviral vector. A combination strategy of targeted vesicles containing papilloma virus or retrovirus DNA molecules might provide a method for increasing the efficiency of expression of targeted molecules.

Particulate systems and polymers for in vitro and in vivo delivery of polynucleotides were extensively reviewed by Felgner in *Advanced Drug Delivery Reviews* 5, 163–187 (1990). Techniques for direct delivery of purified genes in vivo, without the use of retroviruses, has been reviewed by Felgner in *Nature* 349, 351–352 (1991). Such methods of direct delivery of polynucleotides may be utilized for local delivery of either exogenous vav antisense oligonucleotide or artificially-constructed genes producing vav antisense oligonucleotide in situ.

Recently, Wolf et al. demonstrated that direct injection of non-replicating gene sequences in a non-viral vehicle is possible. See *Science*, 247, 1465–1468 (1990). DNA injected directly into mouse muscle did not integrate into the host genome, and plasmid essentially identical to the starting material was recovered from the muscle months after injection. Interestingly, no special delivery system is required. Simple saline or sucrose solutions are sufficient to delivery DNA and RNA.

The vav antisense oligonucleotide may be used as the primary therapeutic for the treatment of the hematologic neoplasm, or may be used in combination with non-oligonucleotide antineoplastic agents. In particular, vav antisense oligonucleotides find utility as bone marrow purging agents. High dose chemotherapy coupled with autologous bone marrow rescue involves removing a portion of the patient's bone marrow, treating the patient with conventional chemotherapy or radiation to substantially destroy the remaining malignant bone marrow cells, treating the stored bone marrow with a vav antisense oligonucleotide, and returning the treated cells to the patient. The treated cells, when returned to the patient, may be stimulated by various known hematopoietic growth factors to repopulate the bone marrow with cells which do not carry the oncogenic transcript.

According to a method for bone marrow purging, bone marrow is harvested from a donor by standard operating room procedures from the iliac bones of the donor. Methods of aspirating bone marrow from donors are well-known in the art. Examples of apparatus and processes for aspirating bone marrow from donors are disclosed in U.S. Pat. Nos. 4,481,946 and 4,486,188. Sufficient marrow is withdrawn so that the recipient, who is either the donor (autologous transplant) or another individual (allogeneic transplant), may receive from about $4 \times 10^8$ to about $8 \times 10^8$ processed marrow cells per kg of body-weight. This generally requires aspiration of about 750 to about 1000 ml of marrow. The aspirated marrow is filtered until a single cell suspension, known to those skilled in the art as a "buffy coat" preparation, is obtained. This suspension of leukocytes is treated with vav antisense oligonucleotides in a suitable carrier, advantageously in a concentration of about 50–200 µg/ml.

Alternatively, the leucocyte suspension may be stored in liquid nitrogen using standard procedures known to those skilled in the art until purging is carried out. The purged marrow can be stored frozen in liquid nitrogen until ready for use. Methods of freezing bone marrow and biological substances are disclosed, for example, in U.S. Pat. Nos. 4,107,937 and 4,117,881.

Other methods of preparing bone marrow for treatment with vav antisense may be utilized, which methods may result in even more purified preparations of hematopoietic cells than the aforesaid buffy coat preparation.

One or more hematopoietic growth factors may be added to the aspirated marrow or buffy coat preparation to stimulate growth of hematopoietic neoplasms, and thereby increase their sensitivity to the toxicity of the antisense oligonucleotide. Such hematopoietic growth factors include, for example, IL-3 and granulocyte macrophage colony stimulating factor (GM-CSF). The recombinant human versions of such growth factors are advantageously employed.

After treatment with the antisense oligonucleotides, the cells to be transferred are washed with autologous plasma or buffer to remove unincorporated oligomer. The washed cells are then infused back into the patient. Other methods for bone marrow purging utilizing antisense oligonucleotide are disclosed in U.S. Pat. No. 5,087,617.

According to a preferred treatment regimen for bone marrow purging, the aspirated bone marrow is contacted daily or twice daily for approximately one to four days with an amount of antisense oligonucleotide effective to overcome the malignant phenotype.

For in vivo administration, the amount of antisense oligonucleotide may vary depending on the nature and extent of the neoplasm, the particular oligonucleotide utilized, and other factors. The actual dosage administered may take into account the size and weight of the patient, whether the nature of the treatment is prophylactic or therapeutic in nature, the age, health and sex of the patient, the route of administration, whether the treatment is regional or systemic, and other factors. Intercellular concentrations of from about 1 to about 200 µg/ml may be employed, preferably from about 10 µg/ml to about 100 µg/ml. The patient should receive a sufficient daily dosage of antisense oligonucleotide to achieve these intercellular concentrations of drug. An effective human intravenous dosage, based upon animal studies employing antisense oligonucleotides targeting other proto-oncogenes in antileukemic therapy, is about 0.4 mg/kg/day. Greater or lesser amounts of oligonucleotide may be administered, as required. Those skilled in the art should be readily able to derive appropriate dosages and schedules of administration to suit the specific circumstance and needs of the patient. It is believed that a course of treatment may advantageously comprise infusion of the recommended daily dose as a continuous intravenous infusion over 7 days. The oligonucleotide may be given for a period of from about 3 to about 28 days, more preferably from about 7 to about 10 days. Those skilled in the art should readily be able to determine the optimal dosage in each case. For modified oligonucleotides, such as phosphorothioate oligonucleotides, which have a half life of from 24 to 48 hours, the treatment regimen may comprise dosing on alternate days.

For ex vivo antineoplastic application, such as, for example, in bone marrow purging, the vav antisense oligonucleotides may be administered in amounts effective to kill neoplastic cells. Such amounts may vary depending on the extent to which malignant cells may have metastasized to the bone marrow, the particular oligonucleotide utilized, the relative sensitivity of the neoplastic cells to the oligonucleotide, and other factors. Concentrations from about 10 to 200 µg/ml per $10^5$ cells may be employed, preferably from about 40 to 150 µg/ml per $10^5$ cells. Supplemental dosing of the same or lesser amounts of oligonucleotide are advantageous to optimize the treatment. Thus, for purging bone marrow containing $2\times10^7$ cell per ml of marrow volume, dosages of from about 2 to 40 mg antisense per ml of marrow may be effectively utilized, preferably from about 8 to 24 mg/ml. Greater or lesser amounts of oligonucleotide may be employed.

The effectiveness of the treatment may be assessed by routine methods which are used for determining whether or not remission has occurred. Such methods generally depend upon some combination of morphological, cytochemical, cytogenetic, immunologic and molecular analyses. In addition, remission can be assessed genetically by probing the level of expression of the vav oncogene. The reverse transcriptase polymerase chain reaction methodology can be used to detect even very low numbers of mRNA transcript.

Typically, therapeutic success is assessed by the decrease in the extent of the primary and any metastatic diseases lesions. For solid tumors, decreasing tumor size is the primary indicia of successful treatment. Neighboring tissues should be biopsied to determine the extent to which metastasis has occurred. Tissue biopsy methods are known to those skilled in the art. For non-solid tumors, i.e. the leukemias, treatment is monitored primarily by histological examination of the bone marrow for surviving leukemic cells. However, a significant number of leukemic cells may still exist when marrow examination provides normal results. For this reason, more recent methods for detecting leukemic cells have focused on detecting the presence of the gene for the relevant oncogene, or its corresponding mRNA, in cells of the bone marrow as a more sensitive test. See for example the following U.S. Pat. Nos.: 4,681,840, 4,857,466 and 4,874,853. The presence of even a few copies of the target oncogene can be effectively detected by amplification using reverse transcriptase polymerase chain reaction technology. For a detailed discussion of such methods, see for example, *Cancer: Principles & Practice of Oncology*, edited by V. T. DeVita, S. Hellman and S. A. Rosenberg, J. B. Lippincott Company, Philadelphia, Pa. (3rd ed., 1989). Methods for diagnosing and monitoring the progress of neoplastic disorders vary depending upon the nature of the particular disease.

An antileukemic treatment plan is proposed as follows. Vav phosphorothioate antisense oligonucleotide (24-mer) is administered as a 24-hour continuous intravenous infusion over 7 days. The oligonucleotide is placed in 5% dextrose water and given at a daily dose ranging from about 0.30 to about 2.0 mg/kg/day. Bone marrow aspiration/biopsy is conducted 7, 14 and 21 days after the first cycle of therapy. The patient is evaluated for response on day 21. Additional cycles of therapy may be performed. For such additional cycles of therapy, a bone marrow biopsy will be performed 21 days after the initiation of therapy. Complete remission is determined by the presence of all of the following for a period of at least 4 weeks: (1) a white count below 10,000/mm$^3$ with granulocytes >1,000/mm$^3$; (2) a platelet count of $\geq$100,000/mm$^3$; (3) absence of leukemic blasts from the peripheral blood; (4) a cellularity of bone marrow biopsy of$\geq$20%, with maturation of all cell lines; (5) $\leq$5% blasts in the bone marrow; (6) the absence of detectable Auer rods; (7) the absence of organomegaly; (8) the absence of extramedullary leukemia, such as central nervous system or soft tissue involvement.

The practice of the invention is illustrated by the following non-limiting examples.

EXAMPLE

Effect of vav Antisense Oligonucleotide Exposure on Normal and Malignant Hematopoietic Progenitor Cell Growth The effect of vav antisense oligonucleotide on hematopoietic progenitor cell cloning efficiency and development was systematically investigated by assessing growth after oligomer exposure: colony-forming unit-erythroid (CFU-E), burst-forming unit-erythroid (BFU-E), colony-forming unit-granulocyte/macrophage (CFU-GM), and colony-forming unit-megakaryocyte (CFU-MEG).

Cells: Human bone marrow cells (BMC) or peripheral blood cells (PB) were obtained from normal healthy, or acute or chronic myelogenous leukemia (AML, CML), volunteers by Ficoll-Hypaque density gradient centrifugation, and were partially enriched for hematopoietic progenitors by positively selecting CD34$^+$ cells with immunomagnetic beads (Dynal A. S., Oslo, Norway). The CD34$^+$ cells were suspended in supplemented alpha medium and incubated with mouse anti-HPCA-I antibody in 1:20 dilution, 45 minutes, at 4° C. with gentle inverting of tubes. Cells were washed×3 in supplemented alpha medium, and then incubated with beads coated with the Fc fragment of goat anti-mouse IgG$_1$ (75 µl of immunobeads/10$^7$ CD34$^+$MNC). After 45 minutes of incubation (4° C.), cells adherent to the beads were positively selected using a magnetic particle concentrator as directed by the manufacturer.

Oligodeoxynucleotides

Unmodified, 18-nucleotide oligodeoxynucleotides (oligomers) were synthesized as previously reported (Gewirtz et al., *Science* 242, 1303–1306 (1988)). In brief, oligomers were synthesized on an Applied Biosystems 380B DNA synthesizer by means of a β-cyanoethyl phosphoramidite chemistry. Oligomers were purified by ethanol precipitation and multiple washes in 70% ethanol. They were then lyophilized to dryness and redissolved in culture medium prior to use at a concentration of 1 µg/µl (170 µM). Oligomer sequences employed, corresponding to codons 2–7 of the translated portion of published vav proto-oncogene cDNA sequence, were as follows: (SEQ ID NO:3), sense oligomer; (SEQ ID NO:2), antisense oligomer; and (SEQ ID NO:4), scrambled sequence oligomer.

Oligomer Treatment of Cells

Cells were exposed to oligomers as previously described (Gewirtz et al., *Science* 242, 1303–1306 (1988)). 2×10$^4$ CD34$^+$MNC were incubated in 5 ml polypropylene tubes (Fisher Scientific, Pittsburgh, Pa.) in a total volume of 0.4 ml of Iscove's modified Dulbecco's medium (IMDM) containing 2% human AB serum and 10 mM Hepes buffer. Oligomers were added at time zero (20–100 µg/ml), and 50% of the initial dose was added again 18 hours later (final total concentration ~5–26 µM). Twenty-four hours after the first addition of oligomers, cells were prepared for plating in plasma clot or methylcellulose cultures. Cells (1×10$^4$ CD34$^+$ MNC per dish) were not washed before plating. Control cultures were manipulated in an identical manner but were not treated with oligomers.

Colony Assays

Assays for hematopoietic progenitor cells of varying lineages were carried out essentially as reported (Id.). In brief, cells (2×10$^4$ CD34$^+$MNC) were resuspended in IMDM supplemented with 30% human AB serum, 1% BSA, $10^{-4}$ M mercaptoethanol, and 10% citrated bovine plasma (Hyclone Laboratories, Denver, Colo.). Addition of the appropriate recombinant human growth factors allowed for stimulation of the following cell types:

CFU-E: 5 U/ml EPO;

BFU-E: 20 U/ml IL-3 and 5 U/ml EPO, or 100 ng/ml SCF and 5 U/ml EPO;

CFU-GM: 20 U/ml IL-3 and 5 ng/ml granulocyte-macrophage colony stimulating factor;

CFU-MEG: 20 U/ml IL-3 and 100 ng/ml IL-6.

One ml volumes were cultured in 35 mm petri dishes at 37° C., 5% $CO_2$, and 95% humidity. CFU-E colonies were scored at day 7, BFU-E colonies at day 14, CFU-MEG at day 12, and CFU-GM at day 11 of incubation. Colony identification was carried out as previously described (Id.).

Statistics

Statistical significance of differences between means of test groups was assessed by Mann-Whitney non-parametric analysis using a statistical software package (Instat, Graph Pad Software, Inc., San Diego, Calif.; StatView 4.0 Abacus Concepts, Berkley, Calif.).

Results

In normal CD34$^+$MNC exposed to vav oligomer erythroid colony formation was inhibited specifically by the antisense sequence (62±16%) in comparison to control (mean±SD; n=3). No effect was seen on CFU-GM or CFU-Meg colony formation, regardless of the sequence employed (n=3). In CD34+ cells isolated from the leukemia patients, CFU-GM colony formation was inhibited ½ AML patients and ¹¹⁄₁₅ CML patients in dose and sequence dependent manner. At 26 µM, the highest antisense oligomer concentration employed, CFU-GM colony formation was inhibited 55±16% and 86±2% (mean±SD) in the AML and CML patients, respectively. Considering all responders as a group, there was no statistically significant difference in colony formation between control cells and either sense-treated or scrambled sense-treated cells (P>0.05). The difference in colony formation as between antisense-treated cells and control, sense-treated or scrambled sense-treated cells was highly significant (P<0.0001).

Reverse Transcription-Polymerase Chain Reaction (RT-PCR)

As additional proof that the antisense effect was due to a specific decrement in vav mRNA levels, the kinetics of vav message expression in marrow mononuclear cells were examined, and the effect of oligomer exposure on vav mRNA levels was then assessed by the following RT-PCR procedure.

Total RNA was extracted from cells using the quanidine isothiocyanate method of Chirgwin et al., *Biochemistry*, 18, 5294 (1979). Cells (2–5×10⁶) were lysed in 250 µl of guanidine thiocyanate buffer (4M guanidine thiocyanate; 50 mMsodium acetate pH 5.0; 1 mM EDTA; 1M β-mercaptoethanol; 0.5% sarcosyl) and then layered over 250 µl of a cesium chloride (5.7M) cushion in Beckman open-top ultra clear centrifuge tubes (0.8 ml). Tubes were centrifuged (Beckman TL-100 Ultracentrifuge; 100,000RMP; 1.5 hours; 20° C.) and the resulting RNA pellet was resuspended in ~400 µl of water, precipitated with 0.3M potassium acetate, washed twice in 75% ethanol, and then stored at −70° C. until used.

RNA was reverse-transcribed with 500 U of Moloney murine leukemia virus reverse transcriptase (MoMLV-RT) and 50 pmol of a 21-nucleotide oligodeoxynucleotide 3' primer complementary to nucleotides 980–959 (GGAGGT-GATA TTTGAGAACT C; SEQ ID NO:5) of the published vav cDNA sequence. The resulting cDNA fragment was amplified using 5 U of *Thermus aquaticus* (Taq) polymerase and a 21-nucleotide oligodeoxynucleotide 5' primer specific for vav nucleotides 610–631 (CCATCCAGCA GCATTTCTTG A; SEQ ID NO:6). Twenty-five µl of amplified product was electrophoresed on 4% agarose gel and subsequently transferred to a nylon filter. Filters were pre-hybridized, and then probed with a $^{32}$P end-labeled oligonucleotide probe (Caracciolo et al., *Science* 245, 1107–1109 (1989)) corresponding to the 26-nucleotide vav sequence (TTTGATGAAG ACCTGGTAGA GATTCG; SEQ ID NO:7) contained within the amplified region. Autoradiography was performed by exposing filters on Kodak X-ray film at −70° C. using intensifying screens.

CD34$^+$MNC cells were kept for 24 hours at 4° C. in IMDM containing 2% human AB serum, then shifted to 37° C. and stimulated with IL-3 (20 U/ml) and EPO (5 U/ml) in 5% human AB serum. Vav expression was determined at intervals according to RT-PCR. The inhibition of colony formation was found to correlate with antisense sequence-specific downregulation of vav mRNA transcripts.

EXAMPLE 2

Effect of vav Antisense Oligonucleotide Exposure on Lung Cancer Cells

Human small cell lung cancer line A549 (ATCC CRL 185) was propagated in Hanks FK medium with 10% bovine fetal serum. The cells were deposited in a 96-well microtiter plate (40,000 cells/well). Oligonucleotide (sense, antisense, scrambled sense or no oligonucleotide) was added to a concentration of 100 µg/ml at time zero. Cells were counted at day seven. The antisense-treated cells were clearly growth-inhibited:

TABLE 1

| A549 Cell Proliferation Assay | |
| --- | --- |
| Oligonucleotide treatment | Cells/ml × 10⁶ @ day 7 |
| — | 2.19 |
| scrambled sense | 0.73 |
| sense | 1.3 |
| antisense | 0.223 |

EXAMPLE 3

Bone Marrow Purging with vav Antisense Oligonucleotide

Bone marrow is harvested from the iliac bones of a donor under general anesthesia in an operating room using standard techniques. Multiple aspirations are taken into heparinized syringes. Sufficient marrow is withdrawn so that the marrow recipient will be able to receive about 4×10⁸ to about 8×10⁸ processed marrow cells per kg of body weight. Thus, about 750 to 1000 ml of marrow is withdrawn. The aspirated marrow is transferred immediately into a transport medium (TC-199, Gibco, Grand Island, N.Y.) containing 10,000 units of preservative-free heparin per 100 ml of medium. The aspirated marrow is filtered through three progressively finer meshes until a single cell suspension results, i.e., a suspension devoid of cellular aggregates, debris and bone particles. The filtered marrow is then processed further into an automated cell separator (e.g., Cobe 2991 Cell Processor) which prepares a "buffy coat" product, (i.e., leukocytes devoid of red cells and platelets). The buffy coat preparation is then placed in a transfer pack for further processing and storage. It may be stored until purging in liquid nitrogen using standard procedures. Alternatively, purging can be carried out immediately, then the purged marrow may be stored frozen in liquid nitrogen until it is ready for transplantation.

The purging procedure may be carried out as follows. Cells in the buffy coat preparation are adjusted to a cell concentration of about $2\times10^7$/ml in TC-199 containing about 20% autologous plasma. Vav antisense oligodeoxynucleotide, for example, in a concentration of about 8 mg/ml, is added to the transfer packs containing the cell suspension. Recombinant human hematopoietic growth factors, e.g., rH IL-3 or rH GM-CSF, may be added to the suspension to stimulate growth of hematopoietic neoplasms and thereby increase their sensitivity vav antisense oligonucleotide toxicity. The transfer packs are then placed in a 37° C. waterbath and incubated for 18–24 hours with gentle shaking. The cells may then either be frozen in liquid nitrogen or washed once at 4° C. in TC-199 containing about 20% autologous plasma to remove unincorporated oligomer. Washed cells are then infused into the recipient. Care must be taken to work under sterile conditions wherever possible and to maintain scrupulous aseptic techniques at all times.

The present invention may be embodied in other specific forms without departing from the spirit or essential attributes thereof and, accordingly, reference should be made to the appended claims, rather than to the foregoing specification, as indicating the scope of the invention.

All references cited herein with respect to synthetic, preparative and analytical procedures are incorporated herein by reference.

I claim:

1. An oligonucleotide consisting of the nucleotide sequence shown as SEQ ID NO:2.

2. An oligonucleotide according to claim 1 which is an alkylphosphonate oligonucleoside or phosphorothioate oligonucleotide.

3. An oligonucleotide according to claim 1 which is an oligodeoxynucleotide.

4. A method for inhibiting the proliferation of leukemic cells comprising contacting said cells in vitro with an effective amount of an oligonucleotide consisting of the nucleotide sequence shown as SEQ ID NO:2.

5. A method according to claim 4 wherein the oligonucleotide is an alkylphosphonate oligonucleoside or phosphorothioate oligonucleotide.

6. A method according to claim 4 wherein the oligonucleotide is an oligodeoxynucleotide.

7. A method according to claim 4 wherein the leukemic cells are selected from the group consisting of chronic myelogenous leukemia cells and acute myelogenous leukemia cells.

8. A method for inhibiting proliferation of erythroid cells comprising contacting said cells in vitro with an effective amount of an oligonucleotide consisting of the nucleotide sequence shown as SEQ ID NO:2.

9. A method according to claim 8 wherein the oligonucleotide is an alkylphosphonate oligonucleoside or phosphorothioate oligonucleotide.

10. A method according to claim 8 wherein the oligonucleotide is an oligodeoxynucleotide.

11. A method for inhibiting the proliferation of cells of a solid tumor comprising contacting said cells in vitro with an effective amount of an oligonucleotide consisting of the nucleotide sequence shown as SEQ ID NO:2.

12. A method according to claim 11 wherein the tumor is characterized by low level vav expression.

13. A method according to claim 12 wherein the tumor comprises a lung tumor.

14. An artificially-constructed gene comprising a transcriptional promotor segment and a segment containing a vav DNA operatively linked in inverted orientation such that transcription of said artificially-constructed gene produces RNA consisting of the nucleotide sequence shown as SEQ ID NO:2.

15. A gene according to claim 14 wherein the promotor segment comprises SV40 promotor.

16. A method for inhibiting the proliferation of leukemic cells comprising introducing into such cells in vitro an artificially-constructed gene according to claim 15.

17. A method according to claim 16 wherein the artificially-constructed gene is introduced into said cells by transfection, by a transducing viral vector or by microinjection.

18. A method according to claim 16 wherein the malignant hematologic cells are selected from the group consisting of chronic myelogenous leukemia cells and acute myelogenous leukemia cells.

\* \* \* \* \*